United States Patent [19]

Kinsolving

[11] Patent Number: 4,520,132
[45] Date of Patent: May 28, 1985

[54] USE OF UNDECYLENIC ACID TO TREAT HERPES LABIALIS

[75] Inventor: C. Richard Kinsolving, Monroe, N.Y.

[73] Assignee: Pennwalt Corporation, Philadelphia, Pa.

[21] Appl. No.: 423,753

[22] Filed: Sep. 27, 1982

[51] Int. Cl.³ .............................................. A61K 31/20
[52] U.S. Cl. .................................................... 514/560
[58] Field of Search ......................................... 424/318

[56] References Cited

PUBLICATIONS

Physicians' Desk Reference 27th, 1973, p. 1119.
Chemical Abstracts 94:197557g (1981).

*Primary Examiner*—Jerome D. Goldberg

[57] ABSTRACT

Warm-blooded animals are treated for Herpes simplex virus-I by administering to the animal a dosage, effective to alleviate the symptoms of the virus, of undecylenic acid and at least one pharmaceutically acceptable carrier, wherein the compound is in the range of from about 1 to about 95% by weight of the composition.

13 Claims, No Drawings

USE OF UNDECYLENIC ACID TO TREAT HERPES LABIALIS

BACKGROUND OF THE INVENTION

This invention relates to a method of treating *Herpes Simplex* Virus-I (called herpes I) infections of the labial area in mammals and more particularly to a method of treating herpes I infections of the labial area in mammals with an antiviral composition containing undecylenic acid, and at least one pharmaceutically accepted carrier.

*Herpes Labialis* is an acute and recurring painful vesicular eruption of the oral mucosa in the vermilion borders of the lips. The causative agent is herpes virus, type I, and the initial infection usually occurs in childhood. Mild trauma such as sunburn, chapping, or fever may be a predisposing factor for a recurrent eruption; the common name for the lesion is a "cold sore".

The onset of a recurrent lesion is usually a feeling of fullness with a burning or itching sensation on the lips. This occurs before the typical vesicle develops. Vesicular lesions usually exist for several hours before the vesicle breaks or the fluid becomes secondarily infected. The lesions then become yellowish and crusted. The condition is self limiting, symptoms generally subsiding after from about 7 to about 10 days.

No prior art is known which discloses the use of undecylenic acid for the treatment of herpes I.

SUMMARY OF THE INVENTION

This invention is directed to a method of treating herpes I infections of the labial area in mammals comprising administering to the mammal in need of said treatment an effective amount for treating the herpes I virus of a composition of undecylenic acid and at least one pharmaceutically acceptable carrier, wherein the compound is from about 1% to about 95% (preferably 2 to about 25%) by weight of the composition.

DETAILED DESCRIPTION OF THE INVENTION

The undecylenic acid drug of this invention can be administered in the antiviral treatment according to this invention by any means that effects contact of the active ingredient compound with the site of virus infection in the body, after the infection becomes visible. The normal dosage form of the drug is topical application. The dosage form may be a solution, gel, emulsion, suspension, paste, ointment, powder, granule, aerosol product, or other suitable formulation. The dosage of the drug administered will be dependent upon the virus being treated, i.e. herpes I, the frequency of treatment, and the effect desired. Generally in man, a daily topical dosage of active ingredient will be from about 5 milligrams to about 50 milligrams per application, although lower and higher amounts can be used. The dosage is generally administered by repeated topical applications and the frequency of application would depend on the formulation and concentration of undecylenic acid. From 2 to 6 applications per day are usual, but three times per day are preferable.

The active ingredient, the drug, can be employed in useful compositions according to the present invention in such dosage forms as solution, semisolid, solid, and solid form. These dosage forms preferably deliver from about 5 milligrams to about 50 milligrams of active ingredient per application, with a range from about 10 milligrams to about 25 milligrams per application being preferred. In these dosage forms the antiviral composition will contain at least one non-toxic pharmaceutically acceptable carrier for the active ingredient.

Examples of the non-toxic carriers or adjuvants are viscosity enhancers such as bentonite, celluloses (e.g. methylcellulose, ethylcellulose, and carboxy methylcellulose), tragacanth, glyceryl monostearate, cetyl alcohol, stearyl alcohol, synthetic spermaceti, and stearic acid; pH modifiers such as dibasic sodium phosphate, citric acid, and sodium hydroxide; preservatives such as methylparaben, propylparaben, benzoic acid, and benzyl alcohol; stability enhancers such as sodium bisulfite and ascorbic acid; coloring such as food, drug and cosmetic (FD&C) and drug and cosmetic (D&C) colors certified by the Food and Drug Administration (FDA); solvents such as water, alcohol (e.g. ethyl alcohol, propyl alcohol and isopropyl alcohol), polyethylene glycol, and propylene glycol; suspending agents such as kaolin, celluloses (e.g. methylcellulose, ethylcellulose, and carboxy methylcellulose), acacia and tragacanth; emulsifying agents such as glyceryl stearate, decyloleate, cetearyl alcohol, polysorbate 80 and triethanolamine; and humectants such as myristyl myristate.

For effective treatment of Herpes Simplex Virus-I the pharmaceutically acceptable carriers are chosen to allow penetration of an effective concentration of the undecylenic acid at the site of infection. Methods of preparing ointments, creams, lotions and other topical preparations to permit various degrees of tissue penetration are well known in pharmaceutical chemistry and several variations of undecylenic acid formulations are envisaged by this invention. The following typical embodiments of pharmaceutical compositions of this invention are given but are not limiting in any way: (all percentages are by weight of composition)

| Undecylenic Acid Solutions | |
|---|---|
| Undecylenic acid | 10% |
| Propyl alchol | 40% |
| Propylene glycol | 20% |
| Triethanolamine | 2% |
| Polysorbate 80 | 1% |
| Water | 27% |
| Undecylenic Acid Lip Balm | |
| Undecylenic acid | 10% |
| Castor oil | 10% |
| Beeswax (synthetic or natural) | 40% |
| Butyl stearate | 20% |
| Arachidyl propionate | 16.9% |
| Butylated hydroxytoluene | 0.1% |
| Flavor/fragrance | 3% |
| Undecylenic Acid Cream | |
| Undecylenic acid | 10% |
| Sorbitol 70% | 15% |
| polythylene glycol 300 monostearate | 7% |
| Stearic acid | 5% |
| Lanolin, anhydrous | 4% |
| White Petrolatum | 3% |
| Triethanolamine | 3% |
| Methyl paraben | 0.5% |
| Polyoxyethylene laurate | 0.25% |
| Perfumes | 0.25% |
| Water | 50% |

EXAMPLE I

The undecylenic acid was tested for its antiviral activity against herpes I using a method that was developed by Sidwell.

The hair was shaved from both sides of female guinea pigs. These female guinea pigs were then innoculated with the herpes I virus for producing the lesions by spreading the virus over a measured area approximately 10 millimeter square (mm$^2$) and scratching within the area 10 times horizontally and 10 times vertically using an innoculating needle. The guinea pigs were then divided up into groups of five per group. The treating composition (undecylenic acid dissolved in a vehicle of 40% propyl alcohol, 20% propylene glycol and 27% water at a concentration of 1 gram of UDA per ten milliliters of vehicle) was applied topically at the same dosage three times a day for seven days. Each animal was treated daily beginning fifteen hours after innoculation by spraying the skin lesion and surrounding skins with three sprays per lesion per treatment whereby each spray delivered 0.15 grams of solution containing 15 milligrams of undecylenic acid, a dosage of approximately 45 milligrams per treatment. A placebo of the vehicle was similarly applied to a second group of guinea pigs. The animals were observed each day for the ten day period and the lesions, when visible, were measured and scored on the third, sixth, and tenth day. No lesions appeared until the second day after the drug treatment had begun (i.e., 2½ days after innoculation) and lesion measurements were first made on the third day of drug treatment (3½ days after innoculation).

The animals were observed and scored by the same person who equated the severity of the lesion in the animal with an arbitrary number, independent of the size of the lesion. A scale of 0 to 4 was used to score the animals where 0 meant that no lesion was formed (i.e., normal); 1 meant that a faint scab had developed; 2 meant that a moderate scab with a slight blister had developed; 3 meant that a heavy scab with blisters had developed; and 4 meant that a very heavy scab with blisters and new vesicles had developed. The lesions were measured and compared to untreated control values.

Calculations for antiviral activity of the drug were based on the average of the daily average scores for the third, sixth, and tenth days for each group of animals. On the third, sixth, and tenth days the values for the lesion size and lesion severity were measured and the mean average for the groups was recorded in Table I.

The known antiviral compound ribavirin (a 5% solution), was evaluated as a control following the same technique described above.

TABLE I

| | Observations of Lesions on Days Indicated | | | | | |
|---|---|---|---|---|---|---|
| | PLACEBO | | 10% UDA | | 5% RIBAVIRIN | |
| *Days | Size (mm) | Rating | Size (mm) | Rating | Size (mm) | Rating |
| 3 | 14.8 | 2.8 | 11.2 | 1.8 | 9.1 | 1.0 |
| 6 | 13.8 | 1.7 | 10.0 | 1.1 | 9.0 | 1.0 |
| 10 | 7.5 | 0.9 | 0 | 0 | 4.6 | 0.7 |

*after initial innoculation

This data in Table I shows that on the tenth day when using a ten percent (10%) undecylenic acid the lesions had completely healed while the five percent (5%) ribavirin solution treated lesion still exhibited a faint scab; thereafter, the control lesions started to get larger again whereas the lesions treated pursuant to the present invention remained dormant with the ribavirin (control) treatment three lesions recurred after the tenth day.

When an attempt was made to treat animals for herpes I with an ointment which contained 5% undecylenic acid and 20% zinc undecylenate, this ointment had no significant effect on the herpes I virus. The technique used to evaluate the ointment was similar to the described for the 10% undecylenic acid solution except that in half of the animals the virus was introduced by intradermal injection of 0.2 ml of the virus; in the other half of the animals the virus was introduced by spreading the virus on the skin and lightly scratching the skin with 4 horizontal and 4 vertical scratches using a sterile innoculating needle. 20 hours after innoculating the animals with the virus, the drug treatment was begun; the ointment was applied three times a day for seven days. After 21 days of observation, the ointment treated group of animals were no better than the placebo group.

EXAMPLE II

Undecylenic acid was evaluated in vitro against herpes I virus to determine its replication effect.

Green Monkey Kidney tissue cells were grown in micro-Petri dishes in sets of twelve duplicates. These sets of tissue culture plates were innoculated (except the control set) with the herpes I virus and different concentrations of the drug were added to the wells. Then these plates were observed for several days and scored by the same person who equated the severity of the destruction of the cells with an arbitrary numbering system. These plates were rated according to the percentage of cells that were destroyed; hence, the higher the number the better the protection.

Drug concentrations of 1.0, 3.2, and 10.0 micrograms per milliliter were used on different sets of plates for evaluating the various concentrations on the animal tissue cultures. At each of these concentrations the percentage of inhibition of virus growth was observed and recorded in Table II.

Comparative parallel evaluations (as a control) were run on a commercial product called vidarabine.

TABLE II

| Effect of Undecylenic Acid and Vidarabine on Herpes Virus Type I | | |
|---|---|---|
| DRUG CONCENTRATION | *INHIBITION OF HERPES I REPLICATION | |
| μg/ml | Undecylenic Acid | Vidarabine |
| 0.0 (control) | 0 | 0 |
| 1.0 | 74% | 0 |
| 3.2 | 85% | 40% |
| 10.0 | 80% | 70% |

*percent inhibition of virus growth (replication) from untreated control virus growth. Drugs are dissolved in tissue culture growth media.

Table II demonstrates that undecylenic acid is effective for inhibiting the virus growth at 1.0 micrograms per milliliter concentration whereas the vidarabine drug is not effective until the concentration of 3.2 micrograms per milliliter is reached. Furthermore, at the 3.2 micrograms per milliliter concentration the undecylenic acid is twice as effective as vidarabine.

What is claimed is:

1. A method of treating herpes I infection of the labial area in mammals comprising administrating to the mammals in need of said treatment by topical application in the area of said infection of an effective amount for treating said herpes I infection of undecylenic acid.

2. The method of claim 1 wherein the undecylenic acid is applied as a component constituting at least about 10% by weight of a composition of said undecylenic acid and at least one pharmaceutically acceptable carrier.

3. The process of claim 2 wherein said acid and said carrier are in the physical form of a cream.

4. The process of claim 3 wherein said cream comprises sorbitol, polyethylene glycol 300 monostearate, stearic acid, anhydrous lanolin, white petrolatum, triethanolamine, methyl paraben, polyoxyethylene laurate, and water.

5. The process of claim 2 wherein said acid and said carrier are in the physical form of a solution.

6. The process of claim 5 wherein the solution comprises propyl alcohol, propylene glycol, triethanolamine, polyoxyethylene 20 sorbitan monooleate, and water.

7. The process of claim 2 wherein said acid and said carrier are in the physical form of a lip balm.

8. The process of claim 7 wherein the lip balm comprises castor oil, beeswax, butyl stearate, arachidyl propionate and butylated hydroxytoluene.

9. A composition for treating herpes I infection comprising an effective amount for treating herpes I infection in mammals of at least about 10% by weight of undecylenic acid and at least one pharmaceutically acceptable carrier for semi-solid or solid dosage form.

10. The composition of claim 9 wherein said carriers are in the form of a cream.

11. The composition of claim 10 wherein said cream comprises sorbitol, polyethylene glycol 300 monostearate, stearic acid, anhydrous lanolin, white petrolatum, triethanolamine, and water.

12. The composition of claim 9 wherein said carriers are in the form of a lip balm.

13. The composition of claim 12 wherein said lip balm comprises caster oil, beeswax, butyl stearate, and arachidyl propionate.

* * * * *